(12) United States Patent
Okuda

(10) Patent No.: US 11,273,308 B2
(45) Date of Patent: Mar. 15, 2022

(54) ELECTROTHERAPY DEVICE

(71) Applicant: G-WAVE CO., LTD., Ogaki (JP)

(72) Inventor: Hidetoshi Okuda, Ogaki (JP)

(73) Assignee: G-WAVE CO., LTD., Ogaki (JP)

( * ) Notice: Subject to any disclaimer, the term of this patent is extended or adjusted under 35 U.S.C. 154(b) by 8 days.

(21) Appl. No.: 17/003,621

(22) Filed: Aug. 26, 2020

(65) Prior Publication Data

US 2020/0391026 A1 Dec. 17, 2020

Related U.S. Application Data

(63) Continuation of application No. PCT/JP2018/008018, filed on Mar. 2, 2018.

(51) Int. Cl.
*A61N 1/36* (2006.01)
*G16H 40/63* (2018.01)
*A61N 1/04* (2006.01)

(52) U.S. Cl.
CPC ......... *A61N 1/3603* (2017.08); *A61N 1/0492* (2013.01); *G16H 40/63* (2018.01)

(58) Field of Classification Search
CPC ..... A61N 1/3603; A61N 1/0492; G16H 40/63
USPC .......................................................... 607/2
See application file for complete search history.

(56) References Cited

U.S. PATENT DOCUMENTS 6,212,432 B1 * 4/2001 Matsuura ................. A61N 1/32
607/76
2014/0343625 A1 11/2014 O Laighin et al.

FOREIGN PATENT DOCUMENTS

| JP | 2001-527452 A1 | 12/2001 |
| JP | 2006-87759 A | 4/2006 |
| JP | 2011-15723 A | 1/2011 |
| KR | 10-2015-0140072 A | 12/2015 |
| WO | 97/45159 A1 | 12/1997 |

OTHER PUBLICATIONS

Shunnsuke Funase, "Breast is regenerated . . . ! AWG, marvel of "wave therapy"", The Funai Sep. 2016.
Notice of Reason for Refusal for Japanese Patent Application No. 2020-503231, dated Nov. 30, 2021.

* cited by examiner

*Primary Examiner* — Nadia A Mahmood
(74) *Attorney, Agent, or Firm* — Kenichiro Yoshida

(57) ABSTRACT

An electrotherapy device includes a storage unit that stores code data in which a plurality of output frequencies are aligned in order of output and to which a code number is assigned and course data in which the plurality of code numbers are aligned in order of output and to which a course number is assigned, and a controller that extracts the course data from the storage unit based on the input course number, extracts the pieces of code data based on the extracted course data, and controls an output unit to output AC currents of the output frequencies in order based on the pieces of code data, wherein the output unit includes switches (ST1) to (ST4) configured to switch to any one of a first output circuit that outputs the AC currents to at least either of a pad electrode or a mat (12) in which a conductive wiring (12e) is arranged and a second output circuit that outputs the AC currents to a probe (13) having pin electrodes (13e).

1 Claim, 8 Drawing Sheets

FIG. 2A

| CODE NUMBER | CODE DATA | NUMBER OF KINDS OF OUTPUT FREQUENCIES | TIME (min) |
|---|---|---|---|
| 1 | 23.5, 63.5, 74.2, 98.6, 127.8, 668.5, 728.9, ⋯, 9893 | 12 | 36 |
| 2 | 22.6, 64.5, 75.3, 99.4, 128.4, 670.3, 734.6, ⋯, 992.6 | 13 | 39 |
| 3 | 667.6, 728.4, 741.8, 793.3, 882.7, ⋯, 5012 | 13 | 39 |
| 4 | 25.5, 68.3, 75.6, 99.1, 129.4 | 5 | 15 |
| ⋮ | | ⋮ | ⋮ |
| m | 13.5, 24.6 | 2 | 6 |

FIG. 2B

| COURSE NUMBER | COURSE DATA | | | | | | | | NUMBER OF CODE NUMBERS | TOTAL TIME (min) |
|---|---|---|---|---|---|---|---|---|---|---|
| 0 0 | CODE NUMBER | 1 | 2 | 3 | 261 | | | | 4 | 150 |
| | TIME (min) | 36 | 39 | 39 | 36 | | | | | |
| 0 1 | CODE NUMBER | 42 | 67 | 4 | 180 | | | | 4 | 96 |
| | TIME (min) | 33 | 27 | 15 | 21 | | | | | |
| 0 2 | CODE NUMBER | 1 | 60 | 258 | 25 | 284 | | | 5 | 117 |
| | TIME (min) | 36 | 30 | 24 | 15 | 12 | | | | |
| ⋮ | | | | | | | | | | |
| 1 5 | CODE NUMBER | 4 | 119 | 176 | 144 | 30 | 75 | 283 | 340 | 8 | 120 |
| | TIME (min) | 15 | 18 | 27 | 3 | 12 | 21 | 18 | 6 | | |

ELECTROTHERAPY DEVICE

BACKGROUND OF THE INVENTION

Field of the Invention

The present invention relates to an electrotherapy device that outputs an AC (alternating-current) current of a specific frequency.

Description of the Related Art

An electrotherapy device that outputs a current of a predetermined frequency to a pair of pad electrodes attached to a human body has been known. The electrotherapy device of this type is operated by attaching the pad electrodes to a body surface, and then, setting a frequency, output time, and an output voltage.

The existing electrotherapy device however has the problem that when a frequency is desired to be changed in the middle, it takes time and labor because a process of once stopping the operation, selecting a frequency to which the frequency is desired to be changed, and then, operating the electrotherapy device is restrated.

SUMMARY OF THE INVENTION

The present invention has been made in view of the above-described circumferences and an object thereof is to provide an electrotherapy device that can continuously output AC currents of a plurality of different frequencies.

In order to solve the above-described problem, an electrotherapy device according to an aspect of the present invention "includes:

a storage unit that stores code data in which a plurality of output frequencies are aligned in order of output and to which a code number is assigned and course data in which the code numbers are aligned in order of a plurality of the pieces of code data to be output and to which a course number is assigned;

an input operation unit with which the course number is input by an operation by a user;

an output unit including an output circuit that outputs AC currents; and a controller that extracts the course data from the storage unit based on the course number input from the input operation unit, extracts the pieces of code data based on the code numbers forming the extracted course data, and controls the output unit to output the AC currents of the output frequencies in order based on the pieces of extracted code data, wherein the output unit includes a switch configured to switch the output circuit to any one of a first output circuit that outputs the AC currents of the output frequencies to at least either of a pad electrode or a mat in which a conductive wiring is arranged and a second output circuit that outputs the AC currents of the output frequencies to a probe having a pin electrode by an operation by the user.

With this configuration, when the course number is input from the input operation unit, the course data related to the course number and the pieces of code data related to the code numbers forming the course data are extracted from the storage unit. The AC currents are output in the order of the code numbers forming the course data and the order of the output frequencies forming the code data of each of the code numbers. Accordingly, unlike the existing technique, AC currents of a plurality of different frequencies can be continuously output easily with no need of stopping the operation and inputting the output frequency every time the output frequency is switched.

The output circuit can be switched between the first output circuit that outputs the AC currents to at least either of the pad electrode or the mat in which the conductive wiring is arranged and the second output circuit that outputs the AC currents to the probe having the pin electrode. Accordingly, the electrotherapy device can meet a requirement for an electrotherapy device capable of executing varieties of treatments by one device.

In addition to the above-described configuration, in the electrotherapy device in the aspect of the present invention, "an output voltage of the output frequencies is capable of being set by an operation by the user, the controller increases the output voltage to a set value from zero at a constant increase rate regardless of a magnitude of the set value when controlling the output unit to start output of the AC currents of the output frequencies, and the controller lowers the output voltage to zero from the set value at a constant lowering rate regardless of the magnitude of the set value when controlling the output unit to stop the output of the AC currents of the output frequencies."

With this configuration, when the output of the output frequency is started, the output voltage is gradually increased to the set value from zero whereas when the output thereof is stopped, the output voltage is gradually lowered to zero from the set value. The body of the user therefore receives less stimulation with change in the magnitude of the output voltage.

In addition, the output voltage change rates (the increase rate and the lowering rate) are made constant regardless of the magnitude of the set value of the output voltage. The user therefore receives constant stimulation with the change in the output voltage.

Advantageous Effects of Invention

As described above, an electrotherapy device that can continuously output AC currents of a plurality of different frequencies can be provided as an effect of the present invention.

BRIEF DESCRIPTION OF THE DRAWINGS

FIG. 2A is a descriptive view for explaining code data and FIG. 2B is a descriptive view for explaining course data.

DESCRIPTION OF THE EMBODIMENTS

Figure 1:
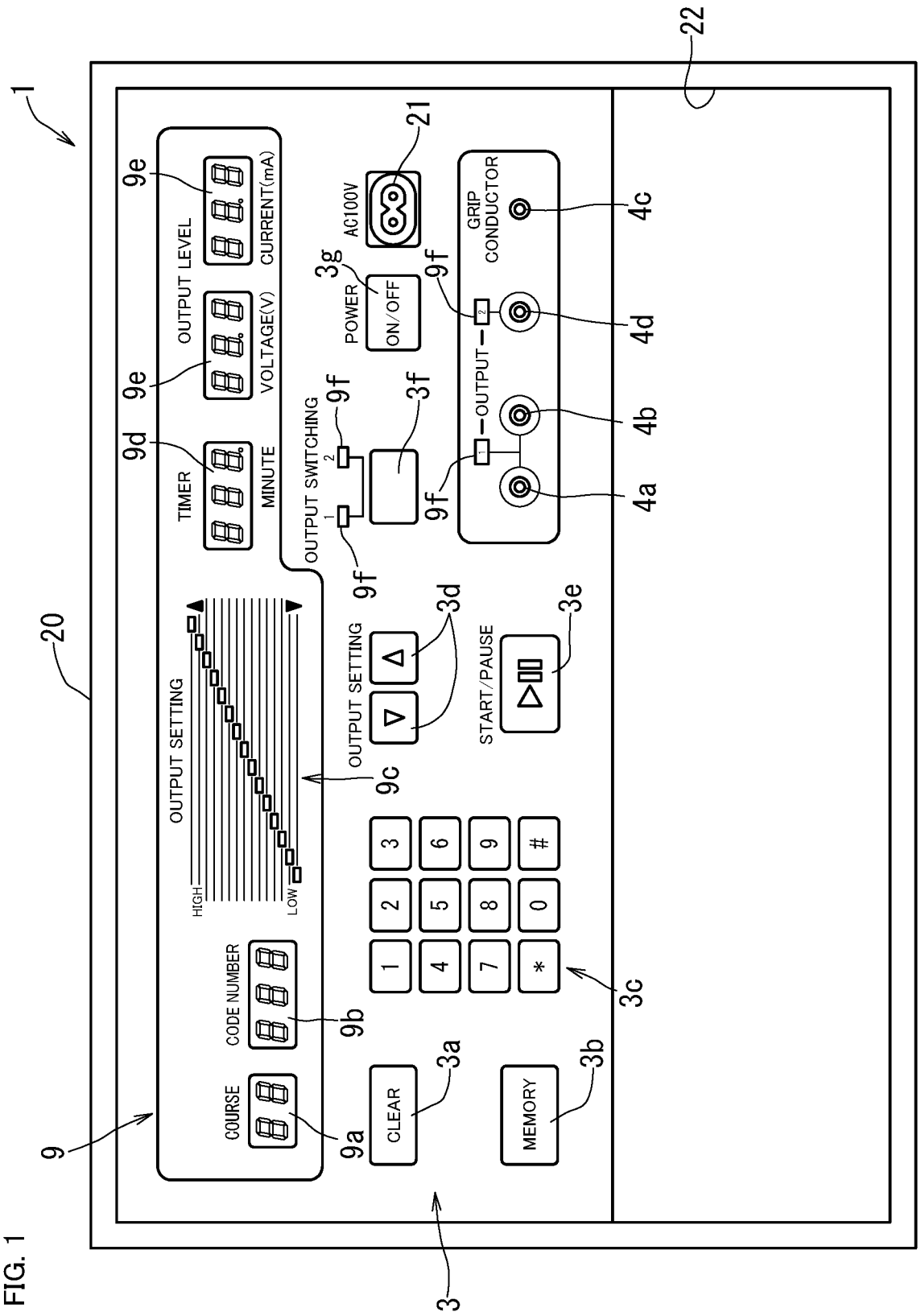
FIG. 1 is a front view of an electrotherapy device according to an embodiment of the present invention.
Figure 3:
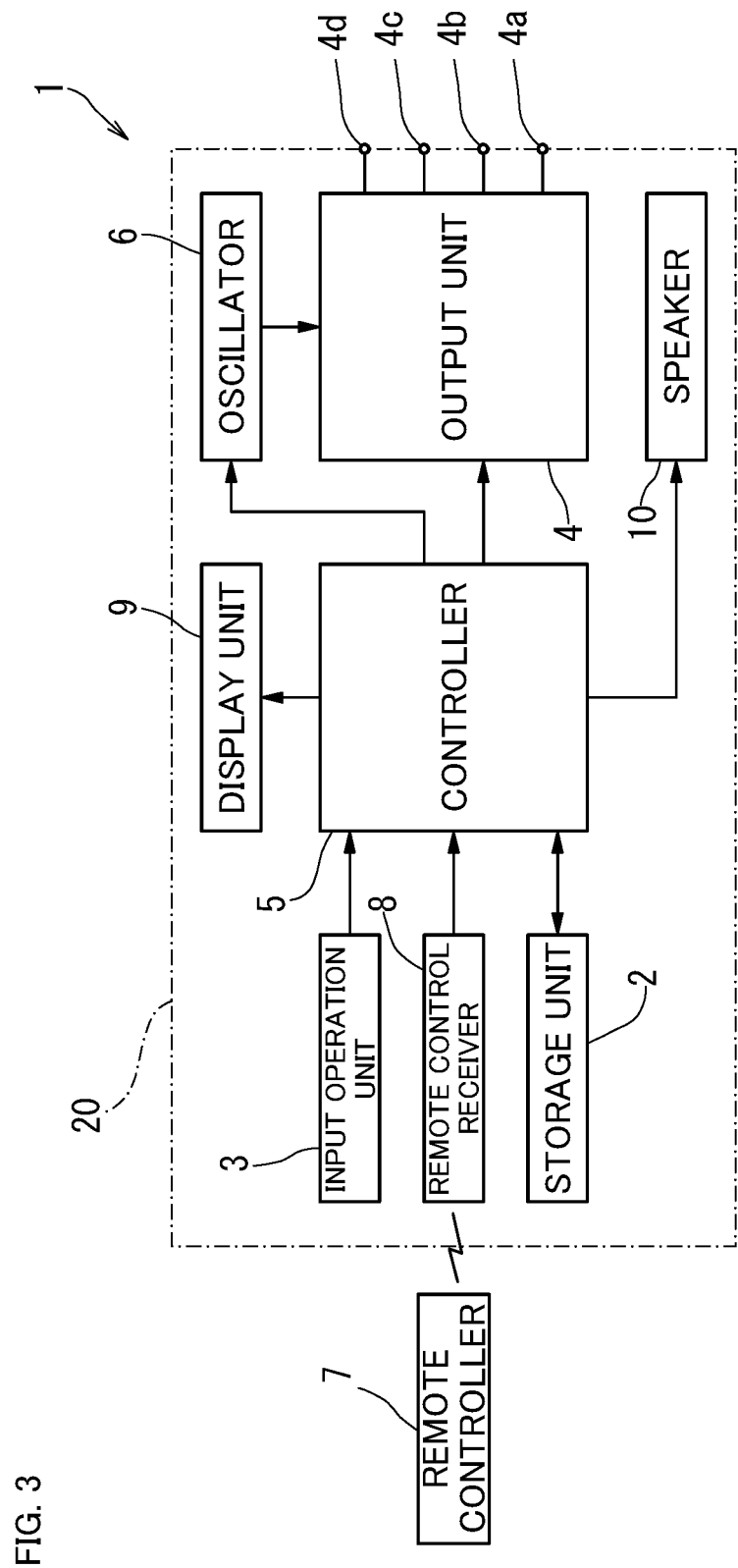
FIG. 3 is a block diagram illustrating the functional configuration of the electrotherapy device in FIG. 1.

An electrotherapy device 1 according to a specific embodiment of the present invention will be described with reference to FIG. 1 to FIG. 8C. The electrotherapy device 1 includes a storage unit 2, an input operation unit 3, an output unit 4, a controller 5, an oscillator 6, a remote control receiver 8, a display unit 9, and a speaker 10.

The electrotherapy device 1 outputs 25 to 200 kinds of output frequencies in a range of 1 to 10000 Hz and stores, in the storage unit 2, output frequencies selected from them as code data and course data. As illustrated in FIG. 2A, the code data is stored as a database in which a plurality of output frequencies are aligned in order of output and that is related to a code number. In the embodiment, the number of kinds of output frequencies forming each code data is 1 to 50, and the output frequencies are aligned in the ascending order of numerical values for each code data. Output time is set to be equal among the output frequencies and is three minutes in this embodiment. In addition to the code data, the number of kinds of output frequencies forming each code data and total output time are stored while being related to the code number. The storage unit 2 stores therein 344 pieces of code data at most.

As illustrated in FIG. 2B, the course data is stored in the storage unit 2 as a database in which the code numbers are aligned in the order of output of the plurality of pieces of code data and that is related to a course number. Each course data is configured by aligning one to eight code numbers such that the total number of kinds of output frequencies is not more than 50. That is to say, the total output time when one course data is executed is equal to or less than 150 minutes. There are course numbers of "00" to "15", and the course data is previously stored so as to be related to each of these course numbers. The course data related to the course number "00" can be stored as a succession of any code numbers by an operation by a user. In addition to the course data, the number of code numbers forming the course data and the total output time are stored in the storage unit 2 while being related to each of the course numbers "00" to "15".

Figure 4A:
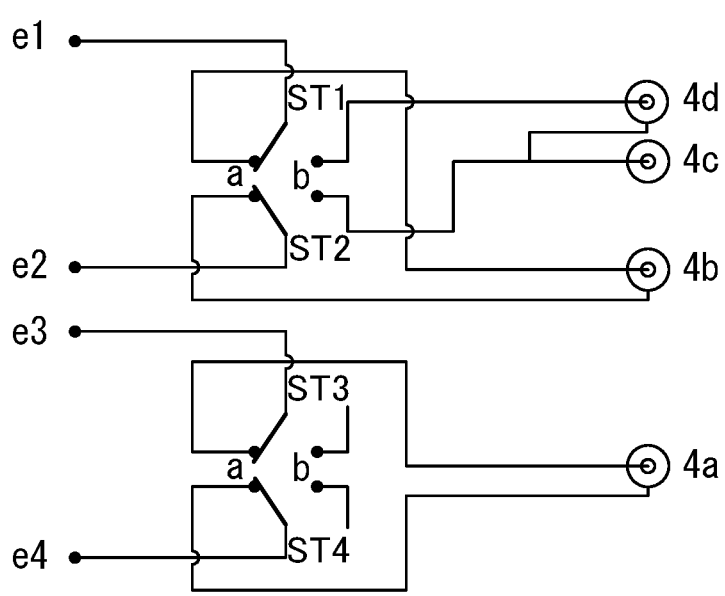
FIG. 4A is a diagram illustrating a main part of an output circuit for illustrating switching between a first output circuit and a second output circuit.

The oscillator 6 generates a waveform of a frequency in accordance with a command from the controller 5. The output unit 4 outputs, to output terminals 4a to 4d, an AC current of a certain frequency generated by the oscillator 6. As illustrated in FIG. 4A, an output circuit of the output unit 4 causes the AC current to flow from a connection portion e1 to a connection portion e2 and causes the AC current having the same frequency as the above to flow from a connection portion e3 to a connection portion e4. In this output circuit, switches ST1, ST2, ST3, and ST4 are simultaneously operated with an operation on an output switch button 3f (which will be described later) by the user. With this operation, the output circuit is switched between a first output circuit that outputs the AC current to the output terminals 4a and 4b with close of connection points a and a second output circuit that outputs the AC current to the output terminals 4c and 4d with close of connection points b.

The remote control receiver 8 receives a signal from a remote controller 7. The remote controller 7 includes a start/pause button and an output level setting button. When the input operation unit 3 is operated and when output of the AC current from the output unit 4 is started/ended, the speaker 10 emits alarm sound.

The storage unit 2, the output unit 4, the controller 5, the oscillator 6, the remote control receiver 8, and the speaker 10 are accommodated in a housing 20 of the electrotherapy device 1. The input operation unit 3 and the display unit 9 are provided on the front surface of the housing 20.

As illustrated in FIG. 1, the input operation unit 3 includes a clear button 3a, a memory button 3b, a ten key 3c, an output level setting button 3d, a start/pause button 3e, the output switch button 3f, and a power supply button 3g. The ten key 3c is configured by 12 buttons of number buttons of "0" to "9", "*", and "#".

The display unit 9 includes a course display portion 9a displaying the course number, a code display portion 9b displaying the code number, an output level display portion 9c displaying an output level, a time display portion 9d displaying output time, output value display portions 9e displaying a voltage value and a current value that are output, and output switch display portions 9f. The course display portion 9a is a two-digit 7 segment LED. Each of the code display portion 9b, the time display portion 9d, and the output value display portions 9e is a three-digit 7 segment LED. On the output level display portion 9c, 15 LEDs are linearly arrayed upward to the right.

Figure 5A:
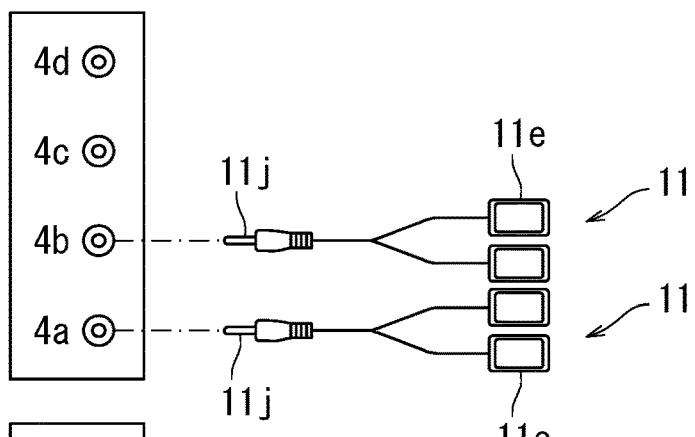
FIG. 5A to FIG. 5D are views for explaining connection of electrode pad pairs, the mat, the probe, and an earth grip to output terminals.
Figure 5B:
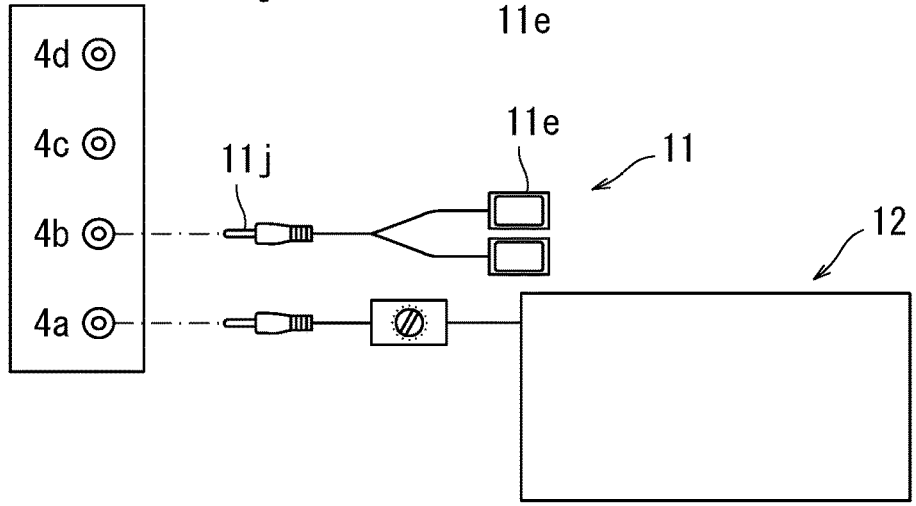

The output terminals 4a to 4d and a power supply terminal 21 for connection with a commercial power supply are mounted on the front surface of the housing 20. Any of an electrode pad pair 11, a mat 12, a probe 13, and an earth grip 14 are connected to the output terminals 4a to 4d. As illustrated in FIGS. 5A and 5B, each electrode pad pair 11 includes a pair of pad electrodes 11e with adhesive pads for being attached to a body surface of a user and a connection terminal 11j that is electrically connected to the pad electrodes 11e and will be connected to the output terminal 4a or the output terminal 4b.

Figure 4B:
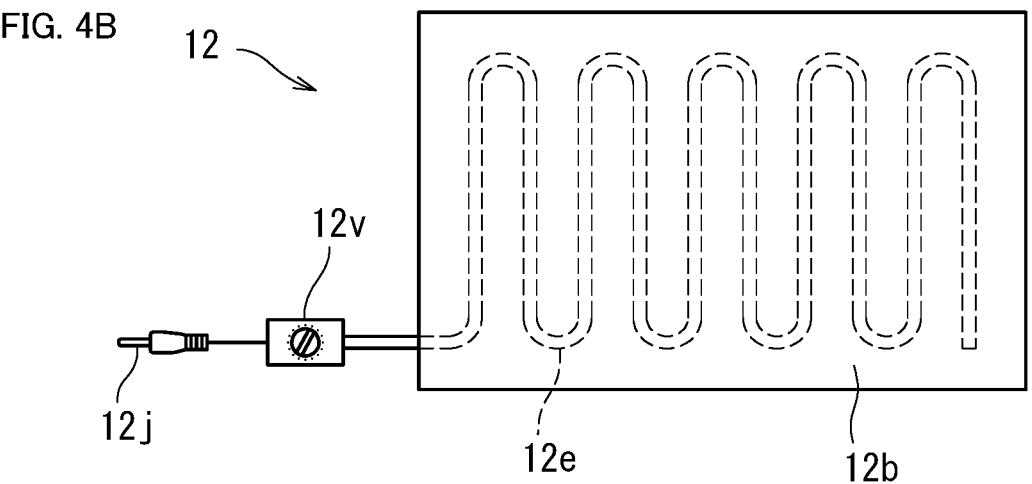
FIG. 4B is a configuration view of a mat.

As illustrated in FIG. 4B, the mat 12 includes a mat main body 12b as an electrically non-conductive flexible sheet, a conductive wiring 12e arranged in a curved manner in the mat main body 12b, and a connection terminal 12j that will be connected to the output terminal 4a or the output terminal 4b. The mat 12 includes a variable resistor 12v for adjusting a magnitude of a DC (direct-current) current that is supplied to the conductive wiring 12e via the connection terminal 12j. The mat main body 12b is used while a person sits or lies thereon and has a rectangular shape having short sides of 90 to 100 cm and long sides of 160 to 200 cm.

Figure 4C:
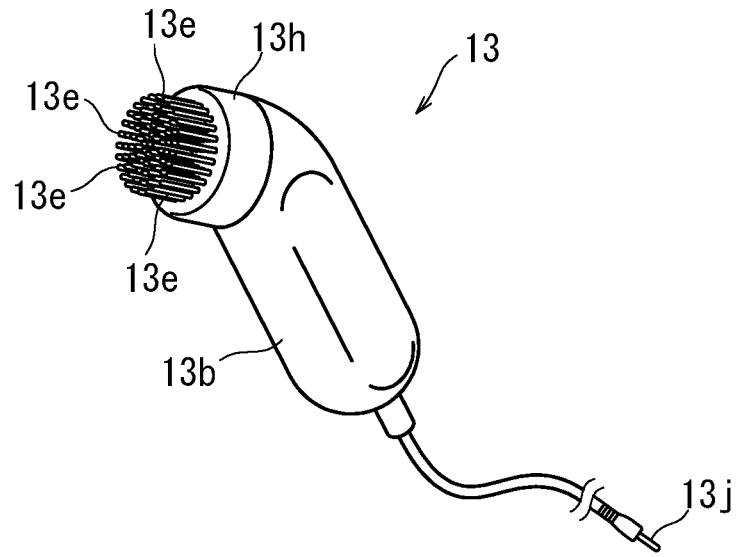
FIG. 4C is a perspective view of a probe.
Figure 5C:
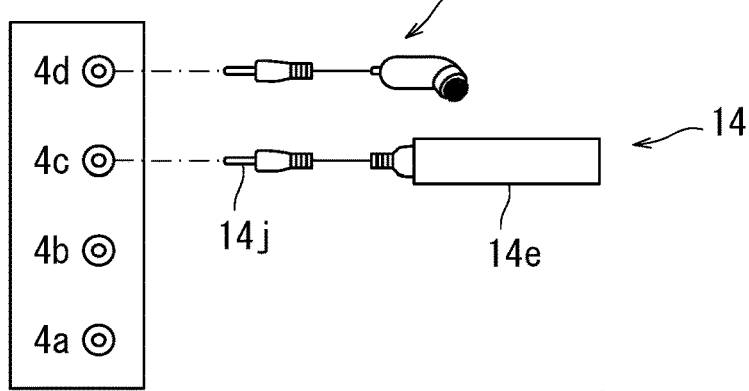
Figure 5D:
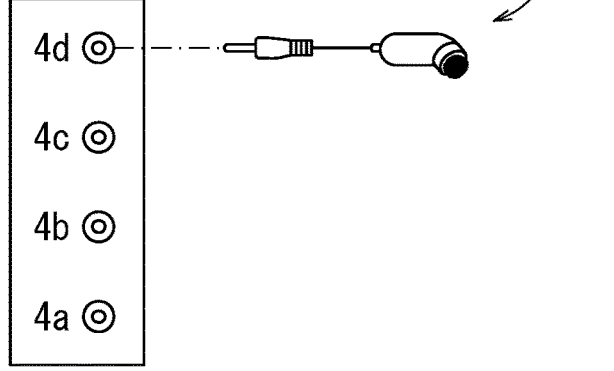

As illustrated in FIG. 4C, the probe 13 includes a probe main body 13b as a portion that the user grips, a head portion 13h provided at the front end thereof, pin electrodes 13e projecting from the head portion 13h, and a connection terminal 13j that is electrically connected to the pin electrodes 13e and will be connected to the output terminal 4d. As illustrated in FIG. 5C, the earth grip 14 includes an electrically conductive shaft 14e and a connection terminal 14j that is electrically connected to the shaft 14e and will be connected to the output terminal 4c.

When the user operates the output switch button 3f of the input operation unit 3, as described above with reference to FIG. 4A, the output circuit is switched to either of the first output circuit or the second output circuit. When switched to the first output circuit, the LED of "1" is lighted on the output switch display portion 9f whereas when switched to the second output circuit, the LED of "2" is lighted.

In the first output circuit, the AC current is output from the output terminal 4a and the output terminal 4b, so that the electrode pad pairs 11 can be respectively connected to the output terminals 4a and 4b as illustrated in FIG. 5A. The AC current having a low frequency can be made to flow through the body of the user using the four electrode pads. Alternatively, as illustrated in FIG. 5B, the electrode pad pair 11 can be connected to one of the output terminal 4a and the output terminal 4b, and the mat 12 can be connected to the other thereof. When the AC current flows through the conductive wiring 12e arranged in the mat main body 12b, a variable magnetic field is generated. When the magnetic field varies, an electric field varies to generate an electromagnetic wave. Accordingly, the body of the user is expected to receive stimulation with the electromagnetic wave and electromagnetic field generated in accordance with the frequency and magnitude of the AC current that is supplied to the conductive wiring 12e.

In the second output circuit, the AC current is output from the output terminal 4c and the output terminal 4d, so that the earth grip 14 can be connected to the output terminal 4c and the probe 13 can be connected to the output terminal 4d as illustrated in FIG. 5C. The probe 13 has the pin electrodes 13e and therefore has an advantage that the electrodes can be made to abut against the body surface even at a place to which the pad electrode is difficult to be attached due to body hair or hair, such as the forearm, lower limb, and scalp. While the user grips the earth grip 14, the AC current of a predetermined frequency can be made to flow through the body of the user between the pin electrodes 13e and the earth grip 14. The probe 13 has an earth portion (not illustrated) at a base of the probe main body 13b. When the user touches the earth portion by operating the probe 13 by himself (herself), the AC current of the predetermined frequency can be made to flow through the body of the user only by connecting the probe 13 to the output terminal 4d without connecting the earth grip 14 to the output terminal 4c.

The electrode pad pairs 11, the probe 13, the earth grip 14, and a power supply code can be accommodated in a recess 22 of the housing 20. The recess 22 is recessed backward below the input operation unit 3 in the front surface of the housing 20.

Next, a method for using the electrotherapy device 1 in the embodiment will be described together with flow of processing in the controller 5. The electrotherapy device 1 has a therapy mode and a course registration mode as operation modes. The therapy mode has three modes of a single code mode in which only one code data related to the code number is executed, a direct mode in which the course data arbitrarily registered for the course number "00" is executed, and a course mode in which the pieces of course data previously set for the course numbers "01" to "15" are executed. The course registration mode is a mode for storing (registering), in the storage unit, the course data to be executed in the direct mode or the course mode.

First, the course registration mode will be described. The storage unit 2 has a region for storing the course data so as to be related to the course number "00" for the direct mode and a region for storing the pieces of course data so as to be respectively related to the course numbers "01" to "15" for the course mode. In factory shipment of the electrotherapy device 1, no data is registered in the region of the course number "00", and different pieces of course data are previously registered in the region of the course numbers "01" to "15". Normally, the arbitrary course data desired by the user can be registered only in the region of the course number "00".

The code registration mode in which the course data is registered for the course number "00" is executed in the following manner. That is, in a state in which the power supply code is connected to the power supply terminal 21 for energization, the power supply button 3g is operated to power ON, and then, the memory button 3b is long-pressed for equal to or more than two seconds. In a state in which no course data is registered for the course number "00", "000" is displayed in a flashing manner on the code display portion 9b whereas when the course data has been already registered, the number at the head of the code numbers forming the course data is displayed on the code display portion 9b.

When the code number is input with the ten key 3c in the state in which "000" flashes on the code display portion 9b, the input figures are displayed on the code display portion 9b. When the button "#" is pressed in this state, the input code number is registered, and the display on the code display portion 9b is switched to flashing of "000" to urge the user to input the next code number. By repeating these operations, the course data formed by eight code numbers at most can be registered. When the eighth code number is registered, registration of the course data is automatically completed. The registration is completed with less than eight code numbers by pressing the button "#" twice.

When the course data that has been already registered for the course number "00" is changed, the code numbers forming the course data can be displayed in order on the code display portion 9b with operations on "Δ" and "∇" of the output level setting button 3d. When a certain code number is desired to be deleted, the corresponding code number is deleted by pressing the clear button 3a in a state in which the code number is displayed, and subsequent code numbers are carried up. When a certain code number is desired to be replaced by another code number, "000" is displayed in the flashing manner on the code display portion 9b by pressing the clear button 3a twice in a state in which the original code number is displayed. The original code number is replaced by a new code number by inputting the new code number with the ten key 3c and pressing the button "#".

Normally, the pieces of registered course data for the course numbers "01" to "15" are locked so as not to be changed. The following procedure can release the locking to allow the pieces of course data registered for the course numbers "01" to "15" to be changed.

First, the power supply code is connected to the power supply terminal 21 to energize the commercial power supply, the memory button 3b is pressed in a state in which the power supply button 3g is in an OFF state, figure buttons "1", "2", and "3" of the ten key 3c are pressed in this order, and then, the power supply button 3g is pressed to power ON. The locking is released with this procedure, so that "01" is displayed in a flashing manner on the course display portion 9a.

In the state in which "01" is displayed in the flashing manner on the course display portion 9a, when the clear button 3a is pressed, and then, the course number that is desired to be changed with the ten key 3c, the corresponding number is displayed in the flashing manner. Thereafter, when the memory button 3b is pressed, the course number to be changed is determined, flashing of the display is stopped, and "000" is displayed in a flashing manner on the code display portion 9b. The course data can be changed and registered with the same procedure as described above for the course number "00". When the change and registration of the course data for the course number are completed, they are locked again.

In the course registration mode, all the code numbers forming one of the course data are collectively deleted by a long-press operation on the clear button 3a for equal to or more than two seconds in the state in which the course number is displayed on the course display portion 9a.

Next, flow of processing in the therapy mode will be described. Any one of the three therapy modes is selected in accordance with an operation manner on the memory button 3b. The course mode is selected with single pressing as the operation on the memory button 3b, the single code mode is selected with double pressing, and the direct mode is selected with long pressing.

Figure 6:
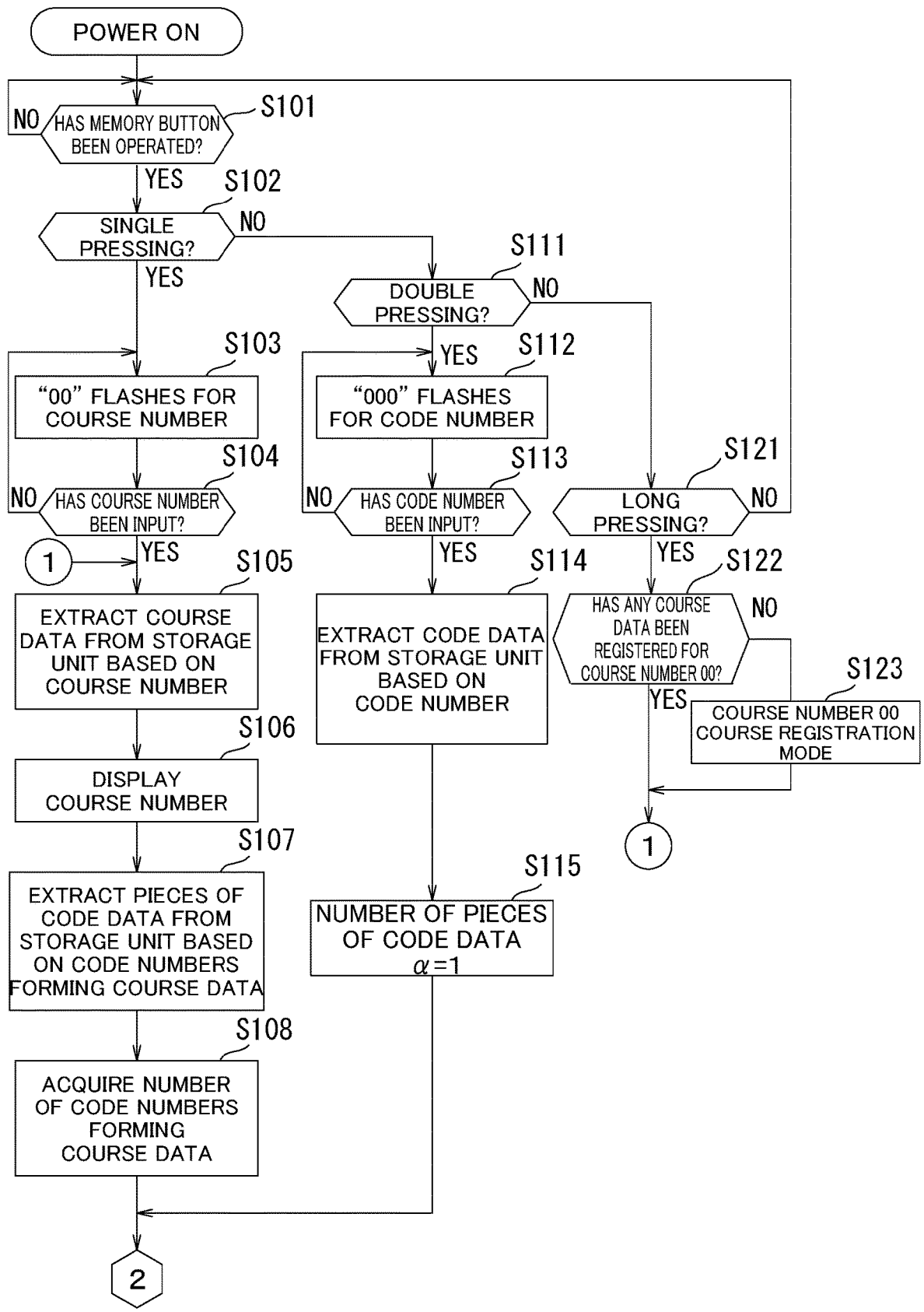
FIG. 6 is a flowchart for explaining flow of processing in a controller.

As illustrated in FIG. 6, when the electrotherapy device 1 is powered ON, first, it is determined whether the memory button 3b has been operated at step S101. The step S101 is repeated until the memory button 3b is operated.

When the memory button 3b has been operated (YES at step S101), it is determined whether the operation is the single pressing at subsequent step S102. When the operation is the single pressing (YES at step S102), the course mode has been selected. Accordingly, "00" is displayed in the flashing manner on the course display portion 9a at step S103 to urge the user to input the course number. The user inputs a desired course number with the ten key 3c and presses the button "#".

It is determined whether the course number has been input at step S104. When any of the figures "01" to "15" have been input, it is determined that the course number has been input, and the process proceeds to subsequent step S105. On the other hand, when figures other than the figures "01" to "15" have been input, it is determined that the course number has not been input, and the process returns to step S103.

At step S105, the course data related to the input course number is extracted from the database. Then, the number at the head of the code numbers forming the course data is displayed on the code display portion 9b at step S106. At step S107, the pieces of code data related to the respective code numbers forming the course data are extracted from the database. Furthermore, at step S108, the number of code numbers (the number of pieces of code data) forming the course data is acquired as a.

On the other hand, when it is determined that the operation on the memory button 3b is not the single pressing at step S102, it is determined whether the operation is the double pressing at step S111. When the operation is the double pressing (YES at step S111), the single code mode has been selected. Accordingly, "000" is displayed in the flashing manner on the code display portion 9b to urge the user to input a code number at step S112. The user inputs a desired code number among "001" to "344" with the ten key 3c and presses the button "#".

It is determined whether the code number has been input at step S113. When any of the figures "001" to "344" have been input, it is determined that the code number has been input, and the process proceeds to subsequent step S114. On the other hand, when figures other than the figures "001" to "344" have been input, it is determined that the code number has not been input, and the process returns to step S112.

At step S114, the code data related to the input code number is extracted from the database. In the single code mode, the number of code numbers is one and "α=1" is therefore set at step S115.

On the other hand, when it is determined that the operation on the memory button 3b is not the double pressing at step S111, it is determined whether the operation is the long pressing at step S121. When the operation is not the long pressing (NO at step S121), none of the course mode, the independent code mode, and the direct mode have been selected, and the process returns to step S101.

When the operation on the memory button 3b is the long pressing (YES at step S121), the direct mode has been selected. Accordingly, it is determined whether the course data has been registered for the course number "00" at step S122. When the course data has been registered, the process proceeds to step S105. On the other hand, when no course data has been registered for the course number "00" (NO at step S122), the course registration mode is executed at step S123 to cause the user to register the course data for the course number "00", and then, the process proceeds to step S105.

Similarly to the above-described course mode, the course data related to the course number "00" is extracted from the database (step S105), and the number at the head of the code numbers forming the course data is displayed on the code display portion 9b (step S106). The pieces of code data related to the respective code numbers forming the course data are extracted from the database (step S107), and the number of code numbers forming the course data is acquired as a (step S108).

When step S108 is ended with the course mode or the direct mode and step S115 is ended with the single code mode, a state in which output in each therapy mode can be started is made. As described above, the user switches to the first output circuit by operating the output switch button 3f to connect the electrode pad pair 11 or the mat 12 to at least one of the output terminals 4a and 4b. Alternatively, the user switches to the second output circuit by operating the output switch button 3f to connect the probe 13 to the output terminal 4d and connect the earth grip 14 to the output terminal 4c if necessary. In addition, the user presses the start/pause button 3e.

Figure 7:
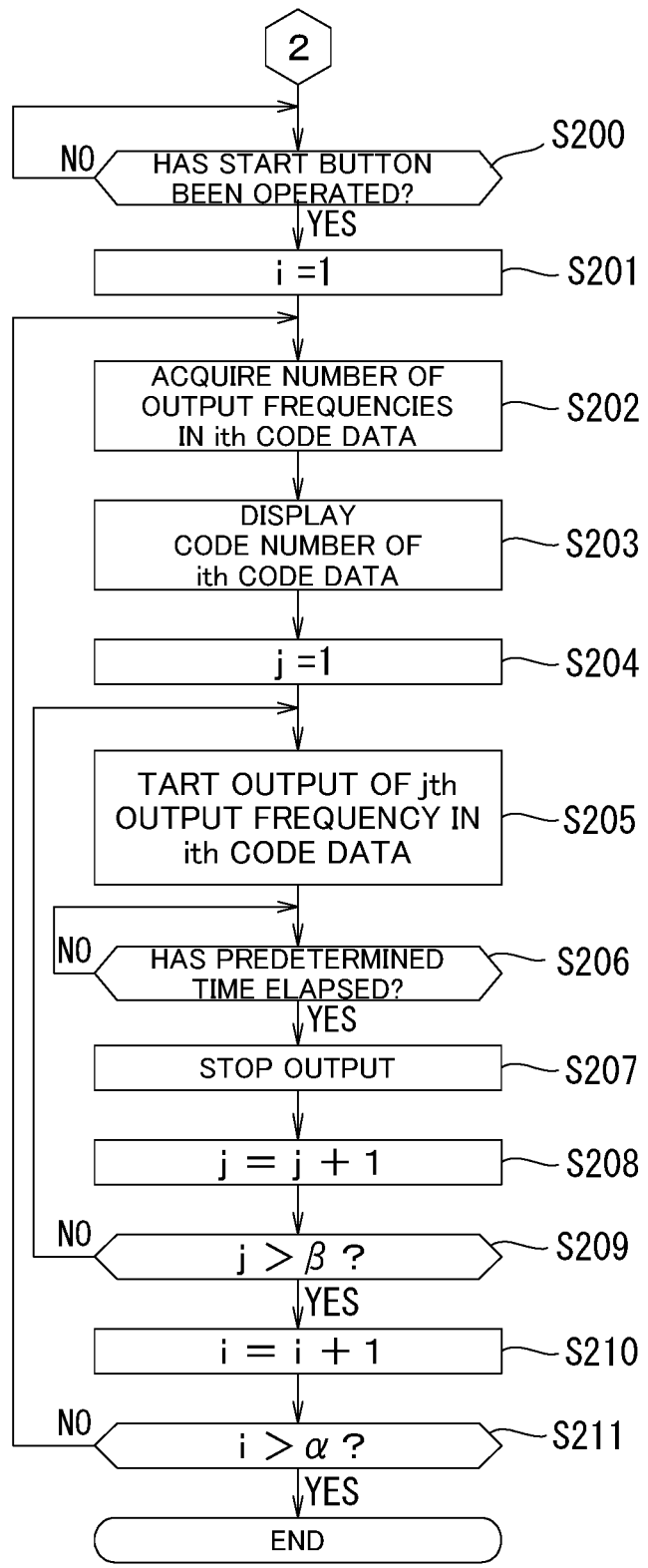
FIG. 7 is a flowchart for explaining the flow of the processing in the controller, which is subsequent to FIG. 6.

As illustrated in FIG. 7, when it is determined that the start/pause button 3e has been pressed at step S200, a value of 1 is set to a variable i at step S201. Then, at subsequent step S202, the number of kinds of output frequencies β forming $i^{th}$ (first) code data is acquired. The code number of the $i^{th}$ code data is displayed on the code display portion 9b at step S203. Further, a value of 1 is set to a variable j at step S204. Thereafter, output of an AC current of a $j^{th}$ (first) output frequency in the $i^{th}$ (first) code data is started at step S205.

It is determined whether predetermined time (three minutes in this embodiment) has elapsed from the start of the output at subsequent step S206. When the predetermined time has elapsed (YES at step S206), the process proceeds to step S207, and the output of the frequency is stopped. 1 is added to the value of j at subsequent step S208, and it is determined whether the value of j is more than β, that is, whether all the output frequencies forming the code data have been output at step S209.

When it is determined that the value of j is not more than β (NO at step S209), the process returns to S205, and output of the AC current of the (second) output $j^{th}$ frequency in the $i^{th}$ (first) code data is started. As in the above-described manner, after the predetermined time has elapsed (YES at step S206), output of the frequency is stopped (step S207), 1 is added to the value of j (step S208), and it is determined whether the value of j is more than β (step S209).

The pieces of processing at step S205 to step S209 are repeated until the value of j is more than β. That is to say, all of β output frequencies included in the $i^{th}$ (first) code data are output in order. When it is determined that the value of j is more than β at step S209, 1 is added to the value of i at step S210, and it is determined whether the value of i is more than α at step S211. In the case of the single code mode, α as the number of code numbers is 1, and the value of i is more than α at this point (YES at step S211), so that the electrotherapy device 1 finishes the operation. At this time, the alarm sound is output from the speaker 10.

On the other hand, in the case of the course mode or the direct mode, the number of code numbers forming the course data is normally equal to or more than 2, and a relation of "i>α" is not satisfied (NO at step S211). The process therefore returns to step S202, and the number of kinds of output frequencies β forming the $i^{th}$ (second) code data in the course data is acquired. In this case, the value of β is changed to a new value from the previously acquired value. As in the above-described manner, the code number of the $i^{th}$ code data is displayed on the code display portion 9b (step S203), and a value of 1 is set to the variable j (step S204). Thereafter, output of the AC current of the $j^{th}$ (first) output frequency in the $i^{th}$ (second) code data is started (step S205). When the predetermined time has elapsed (YES at step S206), the output of the frequency is stopped (step S207), 1 is added to the value of j (step S208), and it is determined whether the value of j is more than β (step S209).

The pieces of processing at step S202 to step S209 are repeated until the value of j is more than β. When the value of j is more than β (YES at step S209), 1 is added to the value of i (step S210), and it is determined whether the value of i is more than α (step S211). The pieces of processing at step S202 to step S211 are repeated until the value of i is more than α, the α pieces of code data forming the course data are executed in order, and the β output frequencies in each code data are output in order.

When it is determined that the value of i is more than α (YES at step S211), all of the pieces of code data forming the course data are completely executed. Therefore, warning sound is output from the speaker 10, and the electrotherapy device 1 finishes the operation.

The electrotherapy device 1 displays the total output time on the time display portion 9d with selection of the therapy mode, and countdown time is displayed on the time display portion 9d upon the start of the output. In the electrotherapy device 1, while the AC currents of the output frequencies are output based on the code data, the output can be temporarily stopped by pressing the start/pause button 3e. In this state, countdown on the time display portion 9d is stopped, and display (the voltage value and the current value) on the output value display portion 9e is "000". When the start/pause button 3e is pressed in a state where the output is stopped, the output is restarted, and the countdown on the time display portion 9d is restarted.

In the electrotherapy device 1, an output level can be changed by operating the output level setting button 3d in a state in which the code number is displayed on the code display portion 9b in the above-mentioned therapy mode. The output level is obtained by classifying the output voltage into 150 ranks and can be increased or lowered by a unit of one rank. On the output display portion 9c, the number of lighting LEDs is increased by one when the output level is increased by ten ranks, and one of the lighting LEDs is lighted off when the output level is lowered by ten ranks.

The controller 5 gradually increases the output level to a set value from zero when the output of the output frequency is started. Similarly, the controller 5 gradually lowers the output level to zero from the set value also when the output of the output frequency is stopped. Such control of the output level is performed when the output is paused or restarted by the operation on the start/pause button 3e and when the power supply button 3g is turned OFF in addition to when the output frequency is switched based on the code data during execution of the therapy mode.

Figure 8A:
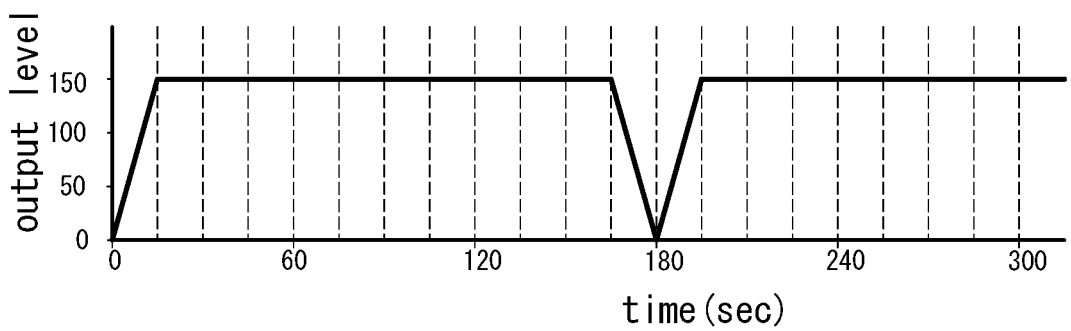
FIG. 8A to FIG. 8C are descriptive views for explaining control of an output level.
Figure 8B:
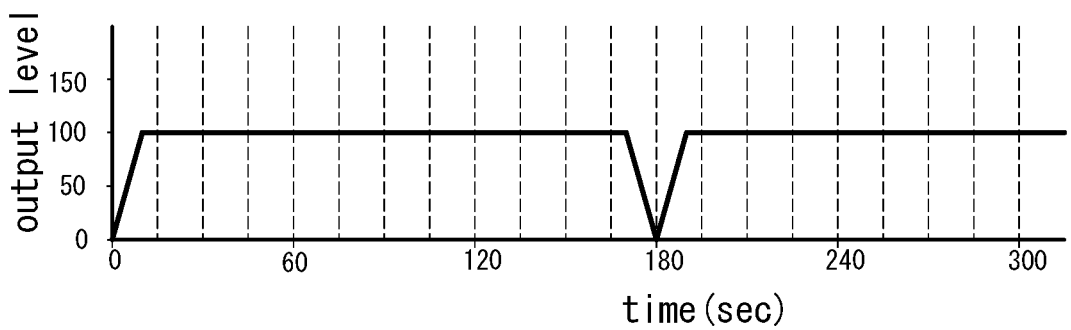
Figure 8C:
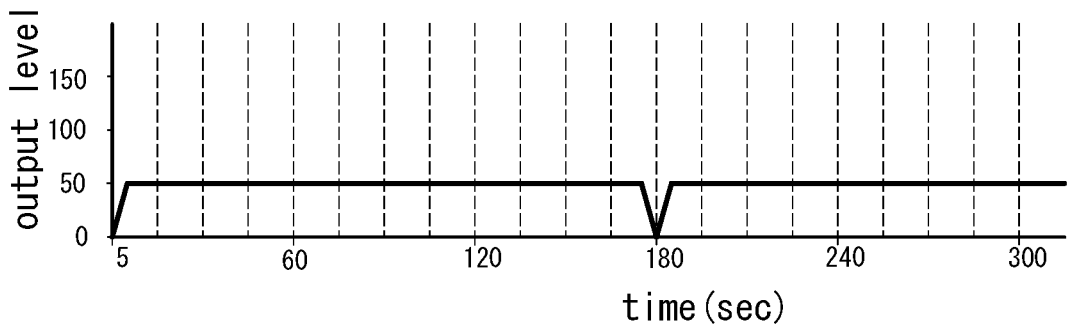

The increase rate of the output level to the set value from zero and the lowering rate thereof to zero from the set value are constant regardless of the magnitude of the set value of the output level, as illustrated in FIG. 8A to FIG. 8C. The increase rate and lowering rate of the output level are set constant regardless of the magnitude of the set value of the output level, so that stimulation received by the body is constant with change in the output level. In the embodiment, the increase rate and lowering rate of the output level are 10 ranks of the output level per second.

The output level can be changed and the output can be paused and restarted with the remote controller 7 in addition to the operation on the input operation unit 3.

As described above, with the electrotherapy device 1 in the embodiment, when the course number is input from the input operation unit 3, the course data related to the course number and the pieces of code data related to the code numbers forming the course data are extracted from the storage unit 2. The AC currents are output in the order of the code numbers forming the course data and the order of the output frequencies forming the code data of each code number. Accordingly, unlike the existing technique, the AC currents of the plurality of different frequencies can be continuously output easily with no need of stopping the operation and inputting the output frequency every time the output frequency is switched.

Further, in the code data related to each code number, the plurality of output frequencies are aligned in the ascending order of numerical values and are output in that order. The stimulation received by the body in switching of the output is thereby made low, and the user feels less discomfort. The AC currents are output such that the output frequencies are sequentially increased. Therefore, the body gradually gets used to the stimulation and feels less discomfort even when the stimulation is increased.

Furthermore, the number of kinds of output frequencies forming each course data is not more than 50. The risk that the user gets tired of increase in required time is thereby reduced.

When the output of the output frequency is started, the output level is gradually increased to the set value from zero whereas when the output thereof is stopped, the output level is gradually lowered to zero from the set value. The body of the user therefore receives less stimulation with the change in the output level. In addition, the output level change rate is made constant regardless of the magnitude of the set value of the output voltage. The user thereby receives constant stimulation with the change in the output voltage.

In addition, in the electrotherapy device 1, the output circuit can be switched to the first output circuit and the second output circuit, and any of the electrode pad pair 11, the mat 12, and the probe 13 can be connected to the output terminals 4a to 4d from which the AC currents are output. With this configuration, the electrotherapy device can meet a requirement for an electrotherapy device capable of executing varieties of treatments by one device.

Although the present invention has been described above using the preferred embodiment, the present invention is not limited by the above-described embodiment and various improvements and changes in design can be made in a range without departing from the gist of the present invention.

For example, although the number of pieces of code data that can be stored is 344 at most in the above-described embodiment, the maximum number thereof may be increased and can be set to 15000 to 20000. With this increase, a selection range of the code data can be expanded, and the number of pieces of course data as a combination of the pieces of code data can be largely increased.

What is claimed is:
1. An electrotherapy device comprising:
a storage unit that stores code data in which a plurality of output frequencies are aligned in order of output and to which a code number is assigned and course data in which the code numbers are aligned in order of a plurality of the pieces of code data to be output and to which a course number is assigned;

an input operation unit with which the course number is input by an operation by a user;

an output unit including an output circuit that outputs AC currents; and a controller that extracts the course data from the storage unit based on the course number input from the input operation unit, extracts the pieces of code data based on the code numbers forming the extracted course data, and controls the output unit to output the AC currents of the output frequencies in order based on the pieces of extracted code data, wherein the output unit includes a switch configured to switch the output circuit to any one of a first output circuit that outputs the AC currents of the output frequencies to at least either of a pad electrode or a mat in which a conductive wiring is arranged and a second output circuit that outputs the AC currents of the output frequencies to a probe having a pin electrode by an operation by the user, wherein an output voltage of the output frequencies is capable of being set by an operation by the user, the controller increases the output voltage to a set value from zero at a constant increase rate regardless of a magnitude of the set value when controlling the output unit to start output of the AC currents of the output frequencies, and the controller lowers the output voltage to zero from the set value at a constant lowering rate regardless of the magnitude of the set value when controlling the output unit to stop the output of the AC currents of the output frequencies.

* * * * *